US005741782A

United States Patent [19]
Brockbank et al.

[11] Patent Number: 5,741,782
[45] Date of Patent: Apr. 21, 1998

[54] ANTIBIOTIC COCKTAIL AND METHOD OF USE

[75] Inventors: Kelvin G.M. Brockbank, Marietta; Steven Goldstein, Atlanta, both of Ga.; Chigoke Adoma, Katy, Tex.; Judith K. Sheldon, Smyrna; Patti E. Dawson, Marietta, both of Ga.

[73] Assignee: Cryolife, Inc., Kennesaw, Ga.

[21] Appl. No.: 626,167

[22] Filed: Mar. 29, 1996

[51] Int. Cl.$^6$ .............................. A61K 31/70; A61F 2/02
[52] U.S. Cl. .............................. 514/31; 514/27; 514/192; 514/383; 623/11
[58] Field of Search .............................. 435/1.1, 1.3, 514; 514/27, 31, 192, 383; 623/11

[56] References Cited

U.S. PATENT DOCUMENTS

| | | | |
|---|---|---|---|
| 4,695,536 | 9/1987 | Lindstrom et al. | 435/1 |
| 4,890,457 | 1/1990 | McNally et al. | 62/65 |

FOREIGN PATENT DOCUMENTS

| | | |
|---|---|---|
| 0424 159 A2 | 4/1991 | European Pat. Off. |
| WO 92/12632 | 8/1992 | WIPO |

OTHER PUBLICATIONS

Maesaki et al. *Antimicrobial Agents and Chemotherapy*, pp. 2843–2845, (Dec. 1994).
Walsh et al. *Antimicrobial Agents and Chemotherapy*, pp. 1361–1364, (Jun. 1995).
Abd–Elfattah et al., Inhibition of adenosine deaminase and nucleoside transport, *Journal of Thoracic and Cardiovascular Surgery*, vol. 105 No. 6, pp. 1095–1105 (1993).
Angell, et al. Durability of The Viable Aortic Allograft, *J. Thoracic Cardiovascular Surgery*, vol. 98 No. 1, pp. 48–56 (1989).
Armiger, Histological Assessment of Orthotopic Aortic Valve Leaflet Allografts: Its Role in Selecting Graft Pre–Treatment, *Pathology*, 15: pp. 67–73 (1983).
Barratt–Boyes, et al., A Review of Aortic Valve Homografts Over a Six and One–Half Year Period, *Annals of Surgery*, vol. 170 No. 3, pp. 483–492 (1969).
Barratt–Boys, et al., Long–term follow–up of patents with the antibiotic sterilized aortic homograft valve inserted freehand in the aortic position, *Therapy and Prevention: Valve Replacement*, vol. 75 No. 4, pp. 768–777 (1987).
Brockbank, Effects of Storage Temperature on Viable Bioprosthetic Heart Valves, *Cryobiology*, 29, pp. 537–542 (1992).
El Khatib, Effect of Storage at 4#C in a Nutrient Medium on Antigenic Properties of Rat Aortic Valve Allografts, *Annals of Thoracic Surgery*, 49: pp. 792–796 (1990).
Fontan, et al., Aortic Valve Homografts in the Surgical Treatment of Complex Malformations, *Journal of Thoracic and Cardiovascular Surgery*, vol. 87 No. 5, pp. 649–657 (1984).
Gonzalez–Lavin, Determining viability of fresh or cryopreserved homograft valves at implantation, *Heart Vessels*, 3: pp. 205–208 (1987).

Heacox, Factors affecting the viability of cryopreserved allograft heart valves, *Cardiac Valve Allografts 1962–1987, Current Concepts on the Use of Aortic and Pulmonary Allografts for Heat Valve Substitutes*, SteinkopffVerlag Darmstadt, Springer–Verlag New York.
Hu, Effects of antibiotics on cellular viability in porcine heart valve tissue, *Cardiovascular Research*, 23: pp. 960–964 (1989).
Hunter, The Use of Bactericidal Concentrations of Antibiotics in Hypothermic Pulsatile Perfusion and the Effects on Canine Renal Autograft Function, *The American Surgeon*, pp. 760–765 (1979).
Jonas, Cryopreserved and fresh antibiotic–sterilized valved aortic homograft conduits in a long–term sheep model, *J. Thorac. Cardiovasc. Surg.*, 96: pp. 746–755 (1988).
Khanna, et al., Homograft aortic valve replacement: seven years' experience with antibiotic–treated valves, *Thorax*, 36: pp. 330–337 (1981).
Kirklin, et al., Intermediate–term Fate of Cryopreserved Allograft and Xenograft Valved Conduits, *Annals Thorac. Surg.*, 44: pp. 598–606 (1987).
Kirklin, Multivariate Analysis of Incremental Risk Factors For Hospital Death From All Causes, *Cardiac Surgery*, pp. 421–422 (1986).
Kramer, et al., Antibacterial and Osteoinductive Properties of Demineralized Bone Matrix Treated with Silver, *Clinical Orthopaedics and Related Research*, 161: pp. 154–162 (1981).
Lang, et al., Biochemical and cellular characterization of cardiac valve tissue after cryopreservation or antibiotic preservation, *J. of Thorac. and Cardiovasc. Surg.*, vol. 108 No. 1, pp. 63–67 (1994).
Lange, Allograft Valve Banking: Techniques and Technology, *Cardiac Reconstruction with Allograft Heart Valves*, Springer–Verlog Publishers, pp. 37–63 (1989).
Lockey, et al., A Method of Sterilizing and Preserving Fresh Allograft Heart Valves, *Thorax*, 27: pp. 398–400 (1972).
McGiffin, et al., Long–Term Results of the Viable Cryopreserved Allograft Aortic Valve: Continuing Evidence for Superior Valve Durability, *Journal of Cardiac Surgery*, 3: Supplement pp. 289–296 (1988).
McGregor, Tissue culture, protein and collagen synthesis in antibiotic sterilized canine heart valves, *Cardiovascular Research*, 10: pp. 389–393 (1976).

(List continued on next page.)

*Primary Examiner*—John Kight
*Assistant Examiner*—Howard C. Lee
*Attorney, Agent, or Firm*—Brinks Hofer Gilson & Lione

[57] ABSTRACT

An antibiotic cocktail for sterilizing tissue comprising amphotericin B and fluconazole as antifungal agents and a plurality of antibacterial agents. The agents are present in amounts effective to substantially inhibit fungal and bacterial growth while substantially maintaining the viability of the tissue. Also, a method of sterilizing a tissue comprising contacting the tissue with the antibiotic cocktails of the invention at a temperature and for a period of time effective to substantially inhibit fungal and bacterial growth while substantially maintaining the viability of the tissue.

13 Claims, No Drawings

OTHER PUBLICATIONS

O'Brien, et al., A Comparison of Aortic Valve Replacement with Viable Cryopreserved and Fresh Allograft Valves, with a Note on Chromosomal Studies, *Journal of Thorac. and Cardiovasc. Surg.*, vol. 94, No. 6, pp. 812–823 (1987).

Parker, et al., Storage of heart valve allografts in glycerol with subsequent antibiotic sterilisation, *Thorax*, 33: pp. 638–654 (1978).

Ng, Effect of preservation on the elasticity of human aortic valve homografts, *Thorax*, 30: pp. 266–270 (1975).

Parker, et al., *Storage of heart valve allografts in glycerol with subsequent antibiotic sterilisation*, *Thorax*, 33: pp. 638–654 (1978).

Raju, et al., Twelve–Hour and Twenty Four–Hour Preservation of Small Bowel Allografts by Simple Hypothermia, *Transplantation* vol. 45 No. 2, pp. 290–293 (1988).

Ross et al., Allograft and Autograft Valves used for Aortic Valve Replacement, *Allograft and Autograft Valves*, pp. 129–171.

Sataloff, Preservation of Otologic Homografts, *The American Journal of Otology* vol. 7 No. 3, pp. 214–217 (1986).

Stark, Do we really correct congenital heart defects? *Journal of Thoracic and Cardiovascular Surgery* vol. 97 No. 1, pp. 1–9 (1989).

Strickett, *Disinfection of Human Heart Valve allografts With* (1983).

Sugimoto, Homografts and Cryopreserved Valves, *Cardiac Surgery*, vol. 1 No. 2, pp. 295–315 (1987).

Tan, The Effects of Sterilization and Storage Treatments on the Stress–Strain Behavior of Aortic Valve Leaflets, *Annals of Thorac. Surg.* vol. 22 No. 2, pp. 188–194 (1976).

Watts, et al., Establishment of a Viable Homograft Cardiac Valve Bank: A Rapid Method of Determining Homograft Viability, *Annals of Thorac. Surg.*, vol. 21 No. 3, pp. 230–236 (1976).

White, et al., Procurement and Transplantation of Colonized Cadaver Skin, *The American Surgeon*, vol. 57 No. 6, pp. 402–407 (1991).

Yankah, et al., Orthotopic Transplantation of Aortic Valve Allografts. Early Hemodynamic Results, *Thorac. Cardiovasc. Surg.*, 32: pp. 92–95 (1984).

ANTIBIOTIC COCKTAIL AND METHOD OF USE

FIELD OF THE INVENTION

This invention relates to a method of decontaminating tissues, such as heart valves, for transplantation while maintaining the viability of the tissue. The invention also relates to an antibiotic cocktail for use in the method.

BACKGROUND OF THE INVENTION

The clinical performance of heart valve allografts has been correlated with the viability of the valve leaflet fibroblasts at transplantation. See, O'Brien et al., *J. Card. Surg.*, 2 (Suppl), 153–167 (1987) and Stark, *J. Thoracic Cardiovasc. Surg.*, 97, 1–9 (1989). Accordingly, the highest viability standards must be maintained throughout the entire processing procedure which includes procurement, transportation, decontamination, freezing, storage, thawing and transplantation.

With respect to the decontamination step, antibiotic cocktails for microbial decontamination of tissue are known. In particular, several antibiotic cocktails are known which contain a plurality of antibacterial agents and a single antifungal agent (amphotericin B or, occasionally, nystatin). See, e.g., Watts et al., *Ann. Thorac. Surg.*, 21, 230–36 (1976); Strickett et al., *Pathology*, 15, 457–62 (1983); Armiger et al., *Pathology*, 15, 67–73 (1983); Kirklin and Barratt-Boyes, *Cardiac Surgery*, 421–22 (1986); Heacox et al., in *Cardiac Valve Allografts 1962–1987*, 37–42 (Yankah et al. eds. 1988); Angell et al., *J. Thorac. Cardiovasc. Surg.*, 98, 48–56 (1989); Lange and Hopkins, in *Cardiac Reconstruction With Allograft Heart Valves*, 37–63 (Hopkins ed. 1989); U.S. Pat. No. 4,890,457; U.S. Pat. No. 4,695,536; and PCT application WO 92/12632.

Amphotericin B is considered to be the most effective antifungal agent available. However, amphotericin B has been found to be toxic to the cells responsible for allograft longevity in patients and has, consequently, been removed from some heart valve decontamination solutions. See Hu et al., *Cardiovasc. Res.*, 23, 960–64 (1989); Lange and Hopkins, in *Cardiac Reconstruction With Allograft Heart Valves*, 37–63 (Hopkins ed. 1989); McNally and Brockbank, *J. Med. Engineer. & Tech.*, 16, 34–38 (1992). As a result, yeast contamination currently leads to the rejection of a significant number of heart valves. See McNally and Brockbank, *J. Med. Engineer. & Tech.*, 16, 34–38 (1992).

SUMMARY OF THE INVENTION

The invention provides an antibiotic cocktail for decontaminating tissue. The cocktail comprises: 1) amphotericin B and fluconazole as antifungal agents; and 2) a plurality of antibacterial agents. The agents are present in the cocktail in amounts effective to substantially inhibit both yeast and bacterial growth while substantially maintaining the viability of the tissue.

The invention also provides a method of decontaminating a tissue comprising contacting the tissue with an antibiotic cocktail according to the invention. The tissue is contacted with the antibiotic cocktail at a temperature and for a period of time effective to substantially inhibit the growth of yeast and bacteria while substantially maintaining the viability of the tissue.

As a result of the use of the antibiotic cocktails of the invention, many tissues previously rejected because of yeast or bacterial contamination can now be used for transplantation. This is a significant achievement in view of the scarcity of tissue available for transplantation.

DETAILED DESCRIPTION OF THE INVENTION

"Amounts effective" is used to mean that each of the agents is present at a sufficient concentration such that the cocktail substantially inhibits yeast and bacterial growth but does not substantially decrease the viability of the tissue being decontaminated. These amounts can be determined by dose response testing as is known in the art using standard microbiological tests and viability tests such as those described below. Preferably the agents are present in the cocktail in amounts which are cidal for yeasts and bacteria frequently isolated from tissue.

"Substantially inhibits" means that the cocktail completely inhibits yeast and bacterial growth in at least 90%, preferably at least 95%, most preferably at least 99%, of the tissues decontaminated with the cocktail. "Completely inhibits yeast and bacterial growth" means that yeast and bacterial growth are not detectable by standard microbiological assays after the tissue has been treated with the cocktail.

Viability can be measured in a number of ways. Preferably, however, the tissue is incubated with a radioactively-labeled amino acid, and the incorporation of the amino acid into proteins is monitored by counting disintegrations per minute (DPM) per unit of tissue. "Substantially maintaining the viability" is, therefore, defined to mean that tissue which has been treated with the cocktail incorporates at least about 85% of the DPM per unit tissue as does tissue not treated with the cocktail.

The antifungal agents used in the cocktails of the invention are amphotericin B and fluconazole. The use of these two antifungal agents in combination substantially inhibits yeast growth while substantially maintaining the viability of tissue to be treated with the agents. This result is quite surprising in view of the reported toxicity of amphotericin B to tissue (see Background section above).

Suitable concentrations of amphotericin B and fluconazole can be determined by dose response testing as is known in the art using standard microbiological tests and viability tests such as those described below. Neither amphotericin B, nor fluconazole, alone substantially inhibits yeast growth at doses which substantially maintain tissue viability, but the combination of these two antifungal agents does. Indeed, it has unexpectedly been found that the combination of amphotericin B and fluconazole has synergistic antiyeast activity (see Examples 14 and 15).

A concentration of from about 0.3 µg/ml to about 2.0 µg/ml of amphotericin B is preferred for use in antibiotic cocktails for sterilizing heart valves. A concentration of fluconazole of from about 50 µg/ml to about 100 µg/ml is preferred for use in antibiotic cocktails for sterilizing heart valves.

The antibacterial agents useful in the practice of the invention are chosen so that the combination of antibacterial agents will be effective against a wide range of bacteria, including gram-negative, gram-positives aerobic and anaerobic bacteria. In addition, the antibacterial agents are chosen so that the combination of agents is effective against bacteria commonly found to contaminate the tissue being treated. Many such bacteria are known (e.g., staphylococci, streptococci and propionibacteria) and others can be identified by standard microbiological tests (see, e.g., Example 19 below). Thus, broad spectrum antibacterial agents from two or more families are preferred. Finally, the combination of antibacterial agents must not substantially decrease the viability of the tissue being treated.

Preferably the plurality of antibacterial agents is chosen from the following families: cephalosporins, glycopeptides, aminoglycosides, lincosamides, beta-lactams and rifamycins. More preferably, the combination of antibacterial agents comprises vancomycin and imipenem, and most preferably vancomycin, imipenem and netilmicin. For the decontamination of heart valves, a combination of 50 µg/ml vancomycin, about 10–100 µg/ml imipenem and about 20–50 µg/ml netilmicin is preferred.

Imipenem is a beta-lactam antibiotic. It is active against most aerobic gram-positive and gram-negative bacteria and most anaerobic gram-positive and gram-negative bacteria.

Vancomycin is a tricyclic glycopeptide. It is active against many gram-positive organisms, including staphylococci, streptococci, enterococci, Clostridium and Corynebacterium. It is inactive against gram-negative bacteria.

Netilmicin is in the aminoglycoside family and is effective against many aerobic gram-negative bacteria and some aerobic gram-positive bacteria. Netilmicin is inactive against most streptococci and most anaerobic bacteria.

The concentrations of the antibacterial agents are chosen to be at least 4 to 8 times the minimum inhibitory concentrations for the targeted bacteria as determined by standard microbiological sensitivity assays. Within these parameters, the concentrations of antibacterial agents can be adjusted as a result of dose response testing on tissue using standard microbiological tests and viability tests such as those described below.

From the foregoing, it can be seen that preferred antibiotic cocktails according to the invention contain amphotericin B, fluconazole, vancomycin, imipenem and netilmicin. For sterilizing heart valves, antibiotic cocktails containing about 0.3–1.0 µg/ml amphotericin B, about 50–100 µg/ml fluconazole, about 50 µg/ml vancomycin, about 10–100 µg/ml imipenem and about 20–50 µg/ml netilmicin are preferred. More preferred is the following cocktail:

1.0 µg/ml amphotericin B,

100 µg/ml fluconazole,

50 µg/ml vancomycin,

96 µg/ml imipenem, and

50 µg/ml netilmicin.

The invention also provides a method of sterilizing a tissue comprising contacting the tissue with an antibiotic cocktail according to the invention. A variety of tissues may be decontaminated in this manner, including heart valves, pericardium, vessels, and musculoskeletal connective tissue. As used herein, the term "musculoskeletal connective tissue" includes tissue such as tendons, ligaments and menisci, and excludes tissue such as bone.

The tissue is contacted with the antibiotic cocktail at a temperature and for a period of time effective to substantially inhibit yeast and bacterial growth while substantially maintaining the viability of the tissue. Such times and temperatures can be determined empirically as is known in the art. It has been found that heart valves can be effectively decontaminated by incubating them in an antibiotic cocktail according to the invention for 24–48 hours at a temperature of 35°–39° C.

EXAMPLES

Example 1

This example describes the testing of four antibiotic cocktails on heart valve tissue.

A. Heart Valve Procurement And Preparation

Heart valves found to be unsuitable for allograft transplantation were allocated for experimental use upon receipt of informed consent from the organ procurement organization responsible for mediating with the donor's family. The heart valves were dissected as described in U.S. Pat. No. 4,890,457.

B. Sterilization

Valve leaflets were cut in half, and each half was incubated in 4 ml of Dulbecco's Modified Eagle Medium (DMEM) (GIBCO) buffered with 25 mM 4-(2-hydroxyethyl)-1-piperazine ethanesulfonic acid (HEPES) and containing 10% fetal bovine serum (hereinafter "Solution B") and antibiotics of the types and at the concentrations indicated below. The antibiotics included two combinations of antibacterial agents designated Cocktail B and Cocktail C having the following formulations:

Cocktail B:

62 µg/ml rifampin

57 µg/ml netilmicin

114 µg/ml vancomycin

136 µg/ml cefotaxime

136 µg/ml lincomycin

Cocktail C:

12 µg/ml imipenem

50 µg/ml vancomycin

In addition, two other cocktails were tested. These cocktails were the same as Cocktails B and C, except that they also contained 100 µg/ml fluconazole.

To prepare a stock solution of rifampin, 600 mg of sterile rifampin were dissolved in 10 ml of sterile water. Rifampin was obtained from Merrell Dow (tradename RIFADIN).

A solution of 100 mg/ml of netilmicin sulfate obtained from Schering-Plough (tradename NETROMYCIN) was used as the stock solution of this antibiotic.

A stock solution of vancomycin was made by dissolving 500 mg of sterile vancomycin hydrochloride in 10 ml of sterile water. Vancomycin hydrochloride was obtained from Eli Lilly & Co. (tradename VANCOCIN HCl).

A cefotaxime stock solution was made by dissolving 2.0 grams of sterile sodium cefotaxime in 3 ml of sterile water. Sodium cefotaxime was obtained from Hoechst-Roussel (tradename CLAFORAN).

A solution of 300 mg/ml of lincomycin hydrochloride obtained from Upjohn (tradename LINCOCIN) was used as the stock solution of that antibiotic.

A stock solution of imipenem was prepared by adding 20 ml sterile saline to a 250 mg bottle of imipenem obtained from Merck & Co. (tradename PRIMAXIN).

Finally, a solution of 2 mg/ml of fluconazole obtained from Pfizer Roerig (tradename DIFLUCAN) was used as the stock solution.

An appropriate amount of each of the stock solutions was added to Solution B to give the final concentrations used in Cocktails B and C and Cocktails B and C plus fluconazole.

Experiment 1: Paired halves of leaflets were treated with either Cocktail B or Cocktail B plus fluconazole. Similarly, paired halves of leaflets were treated with either Cocktail C or Cocktail C plus fluconazole. All of the valve leaflet halves were incubated for 48 hours at 37° C. in the antibiotic cocktails and then cryopreserved.

Experiment #2: Paired halves of leaflets were again used. One half was used as a fresh control and immediately labelled with $^3$H-glycine to determine leaflet fibroblast viability (see below). The other half of each leaflet was incubated in Cocktail B or Cocktail B plus fluconazole. Similarly, one half of another pair was used as a fresh control and the other half was incubated in Cocktail C or Cocktail C plus fluconazole. The antibiotic-treated leaflets were incubated for 48 hours at 37° C. in the antibiotic cocktails and then cryopreserved.

B. Cryopreservation

After the treatments with the antibiotic cocktails were completed, the valve leaflet halves were packaged, cryopreserved and stored as described in U.S. Pat. No. 4,890,457, with modifications to the freezing program so that individual valve leaflet halves could be preserved at a cooling rate of —1° C./minute in ~1.6 ml of cryoprotectant solution. A 1.8 ml Nalge cryovial was used to contain the leaflet tissue. The freezing program takes the tissue from +4° to −80° C. in approx 80 to 90 minutes.

C. Storage

The valve leaflet halves were stored in liquid nitrogen freezer for at least two days, but no more than three weeks, before being thawed.

D. Thawing

The valve leaflet halves were thawed by removing the valve tissue to be thawed from the liquid nitrogen freezer. As quickly as possible, the tissue was transferred to a 37° C. waterbath. When all of the ice had dissolved (about 2 minutes), the cryovial was transferred to a hood, and 4 ml of room temperature lactated Ringers plus 5% dextrose (DBLR) was dispensed into a 5-ml snap-cap tube (Falcon) for each cryovial being thawed. The exterior of the cryovial was rinsed with 70% isopropanol and any excess wiped away before opening. Using sterile forceps, the leaflet tissue was transferred into the tube containing the DBLR. The tissue was allowed to remain in D5LR for 5 minutes.

E. Viability Testing

Tissue viability was assessed by the measurement of $^3$H-glycine incorporation into proteins as follows. The thawed valve leaflet halves were placed in snap-cap tubes (Falcon) containing 16 µCi of tritiated-glycine (DuPont New England Nuclear) in 1 ml of DMEM supplemented with 15 µg/ml ascorbic acid. Radiolabeled glycine incorporation was determined after a 48 hour incubation at 37° C. in an atmosphere consisting of 5% carbon dioxide in air. The tissue was then washed four times with phosphate-buffered saline, dehydrated with ethanol and ether, air dried and weighed. The tissue samples were then rehydrated with 200 µl of water and solubilized by the addition of 500 µl of 1M NaOH. After incubation at 60° C. for 1 hour, the samples were sonicated twice for 20-seconds. The homogenates were centrifuged at 12,000× g, and 100 µl aliquots of the supernatants were placed on glass fiber filter discs (Whatman No. 1822024; Whatman Chemical Separation Inc., Clifton, N.J.). The filter discs were dried, and the proteins precipitated by addition of ice-cold 10% trichloroacetic acid for 30 minutes. This was followed by five ethanol rinses, two ether rinses, and drying. The discs were then placed in 10 ml of scintillation fluid (Cytoscint ES, ICN Biomedicals, Inc., Irvine, Calif.). Tritium incorporation was measured by scintillation counting using a LS1701 (Beckman Instruments, Inc., Palo Alto, Calif.).

In Experiment 1, viability was also assayed by labelling some of the leaflet halves with $^3$H-hypoxanthine for autoradiography. To do so, a solution containing 15 µCi/ml of $^3$H-hypoxanthine (DuPont/NEN) in serum free medium (DMEM) containing 5 mg/100 ml gentamicin (Sigma) and 15 mg/100 ml ascorbic acid (Sigma) was prepared. Each leaflet half was placed in a 5 ml sterile snap-cap tube. Using a micropipettor, 0.75 ml of the $^3$-hypoxanthine solution was added to the tissue in the tube. The tubes were incubated at 37° C. with 5% $CO_2$ for 48 hours. Then, the tritiated medium was decanted, and the tissue was washed twice with 3–4 ml of PBS (GIBCO). Another 3–4 ml PBS was added, and the tubes were incubated for 30 minutes at room temperature before removing the liquid. Then, 3–4 ml of PBS was added to each tube, and the tubes were incubated at 4° C. for 18 to 72 hours. The PBS was decanted, and the tissue transferred to a 7 ml glass scintillation vial. The vial was filled with 10% neutral buffered formalin (Fisher), capped and stored at room temperature until the sample was analyzed by autoradiography performed as follows.

The tissue was soaked in 15% sucrose in 0.1M sodium phosphate buffer, pH 7.4, for 2 hours to overnight. The solution was at room temperature at first and then lowered to 4° C. The tissue was dissected, embedded in a plastic mold with OCT, and then frozen in liquid nitrogen. Frozen sections were cut on a cryostat at 6 microns and thaw mounted on chrome alum coated slides (slides dipped twice in a 37° C. solution containing 3.0 g gelatin-bloom 275 and 0.3 g chromium potassium sulfate in 1000 ml distilled $H_2O$). The slides were dried in 37° C. oven overnight to 48 hours, and the OCT was removed from the sections. The sections were then hydrated in ethanol from 95%, 75% down to 50%. The slides were left in 50% ethanol for 10 minutes, and then rinsed in distilled water for 30 sec. The sections were defatted by dehydrating in ethanol to xylene. The slides were hydrated in the same ethanol solutions down to double distilled water. The slides were placed in 37° C. oven to dry (1 hr. to overnight). Liquid Emulsion Kodak NTB2 was melted in a 40° C. waterbath for 30 minutes and then diluted 1:1 with distilled water. The slides were slowly dipped individually into this diluted emulsion 2 times (6 seconds) and allowed to stand 1 hour or until dry. The boxes were sealed tight and stored in a desiccant in coldroom (4° C.) until the slides were developed.

To develop the slides they were allowed to come to about 14° C. while still sealed (about 11 minutes at room temperature). This avoids condensation on the slides, which reduces the signals. All steps were carried out at a temperature of 14° C. The slides were placed in a glass slide rack and immediately developed for 2.5 minutes in D-19 developer (Kodak Catalog #146 4593). The slides were then rinsed in distilled water for 30 seconds, after which they were fixed in Kodak fixer (Polymax T fixer, Catalog #829–5321) for 5 minutes. The slides were rinsed in running tap water at 14° C., and the temperature of the water was slowly raised to room temperature, 21° C., for 10 minutes. Finally, the slides were counterstained with Harris Hematoxylin (Sigma Cat #HHS-32) and Eosin Y, alcoholic solution (Sigma, Cat. #HT 110-1-32).

The results are shown in the following tables. The incorporation of $^3$H-glycine into proteins is expressed in disintegrations per minute (DPM) per mg of dry tissue. The autoradiography results are expressed as a percentage of live cells counted per total number of cells counted.

| Valve | Experiment 1 | | | |
|---|---|---|---|---|
| | DPM/mg | Autorad | DPM/mg | Autorad |
| | Cocktail C | | Cocktail C Plus Fluconazole | |
| B1126 | 2088 | 78% | 3232 | 79% |
| B1127 | 5996 | 71% | 6322 | 62.5% |
| | Cocktail B | | Cocktail B Plus Fluconazole | |
| B1128 | 1430 | 18% | 1526 | 11% |
| B1129 | 2754 | 28% | 2816 | 27% |

| | | | | Cocktail B | Avg % of |
|---|---|---|---|---|---|
| Valve | Leaflet | Fresh | Cock. B | Plus Fluc. | Cocktail B |
| B1134 | 1 | 1847 | 1589 (86%)* | | |
| | 2 | 2112 | 1882 (89%) | | |
| | 3 | 1826 | | 2244 (123%)* | 129% |
| B1135 | 1 | 1830 | 2114 (116%) | | |
| | 2 | 1536 | | 810 (53%) | 45% |
| | 3 | 2255 | | 1091 (48%) | |
| B1137 | 1 | 2179 | 2674 (123%) | | |
| | 2 | 2776 | 4375 (158%) | | |
| | 3 | 1724 | | 2811 (163%) | 80% |
| B1138 | 1 | 1934 | 3320 (172%) | | |
| | 2 | 1449 | | 3412 (235%) | 85% |
| | 3 | 1499 | | 2250 (150%) | |
| B1139 | 1 | 9765 | 7596 (78%) | | |
| | 2 | 5084 | 5276 (104%) | | |
| | 3 | 10519 | | 3786 (36%) | 59% |
| B1140 | 1 | 2154 | 3804 (177%) | | |
| | 2 | 5530 | | 5483 (99%) | 106% |
| | 3 | 4105 | | 2597 (63%) | |

| | | | | Cocktail C | Avg. % |
|---|---|---|---|---|---|
| Valve | Leaflet | Fresh | Cock. C | Plus Fluc. | Cock. C |
| B1141 | 1 | 2410 | 4955 (206%) | | |
| | 2 | 2287 | | 4714 (206%) | 95% |
| | 3 | 3762 | | 4661 (124%) | |
| B1144 | 1 | 2736 | 4355 (159%) | | |
| | 2 | 5550 | | 5128 (92%) | 112% |
| | 3 | 4752 | | 4611 (97%) | |
| B1147 | 1 | 1526 | 2116 (139%) | | |
| | 2 | 1819 | | 3959 (217%) | 148% |
| | 3 | 1582 | | 2287 (145%) | |
| B1148 | 1 | 4448 | 9922 (223%) | | |
| | 2 | 3144 | 8075 (257%) | | |
| | 3 | 3708 | | 8290 (224%) | 92% |
| B1150 | 1 | 2484 | 5085 (205%) | | |
| | 2 | 2796 | 4999 (179%) | | |
| | 3 | 3139 | | 7109 (226%) | 141% |
| B1151 | 1 | 3938 | 3868 (98%) | | |
| | 2 | 5279 | 7160 (136%) | | |
| | 3 | 4155 | | 6055 (146%) | 110% |

*Percent of fresh

Experiment 1—The results indicate that treatment with Cocktail C containing fluconazole produced valve tissue which was at lease as viable as that after treatment with Cocktail C without fluconazole. This is seen in the scintillation results and the auto-radiography. Cocktail B containing fluconazole is also virtually equivalent to Cocktail B without fluconazole. With Cocktail B, however, the tissue is less viable to begin with.

Experiment 2—On average the Cocktail B containing fluconazole gave results which were 84% of those obtained with Cocktail B not containing fluconazole. On average Cocktail C containing fluconazole gave results which were 116% of Cocktail C without fluconazole. When any of the antibiotic treatments is compared to the fresh tissue values, they are all higher than the fresh tissue.

From the results of Experiments 1 and 2, it can be concluded that 100 μg/ml fluconazole added to Cocktail B or C is not harmful to the tissue.

Example 2

Cocktails containing the following antibiotics in the following concentrations were prepared and tested as described in Example 1.

| | |
|---|---|
| Imipenem | 12 μg/ml |
| Vancomycin | 50 μg/ml |
| Fluconazole | 100 μg/ml |
| Rifampin | 0, 10, 30 or 100 μg/ml. |

Paired valve leaflet halves were used. One half of each leaflet was a control. It was incubated in the antibiotic cocktail which did not contain rifampin. The other half was treated with one of the antibiotic cocktails containing rifampin. The results of the assay for incorporation of $^3$-glycine into proteins are presented in the following table in DPM/mg and percent of control.

| | | | Concentration of Rifampin Added | | | | | |
|---|---|---|---|---|---|---|---|---|
| Valve | Leaflet | Control | 10 μg/ml | % | 30 μg/ml | % | 100 μg/ml | % |
| B1154 | 1 | 2139 | 2053 | 96 | | | | |
| | 2 | 2194 | | | 2065 | 94 | | |
| | 3 | 5176 | | | | | 1673 | 32 |
| B1156 | 1 | 4371 | 4816 | 110 | | | | |
| | 2 | 9792 | | | 9238 | 94 | | |
| | 3 | 8748 | | | | | 3583 | 41 |
| B1157 | 1 | 6924 | 6304 | 91 | | | | |
| | 2 | 4775 | | | 4685 | 98 | | |
| | 3 | 3590 | | | | | 2575 | 72 |
| B1159 | 1 | 4786 | 3566 | 75 | | | | |
| | 2 | 6316 | | | 5774 | 91 | | |
| | 3 | 5705 | | | | | 2891 | 51 |
| B1161 | 1 | 4091 | 3002 | 73 | | | | |
| | 2 | 5310 | | | 2034 | 38 | | |
| | 3 | 3876 | | | | | 1170 | 30 |
| B1162 | 1 | 3232 | 3690 | 114 | | | | |
| | 2 | 2620 | | | 1693 | 65 | | |
| | 3 | 2349 | | | | | 547 | 23 |
| AVG | | | | 93% | | 80% | | 42% |

Example 3

Antibiotic cocktails were prepared and tested as described in Example 1. Paired valve leaflet halves were used. One half of each leaflet was used as a control and treated with the following antibiotic cocktail:

| | |
|---|---|
| Imipenem | 12 µg/ml |
| Vancomycin | 50 µg/ml |
| Fluconazole | 100 µg/ml. |

The other half was treated with one of the following test antibiotic cocktails:

| | |
|---|---|
| Imipenem | 12, 24 or 48 µg/ml |
| Vancomycin | 50 µg/ml |
| Fluconazole | 100 µg/ml |
| Rifampin | 10 µg/ml. |

The results of the assay for incorporation of $^3$H-glycine into proteins are presented in the following table in DPM/mg and percent of control. The columns labeled 12, 24 and 48 µg indicate the amount of imipenem per ml used in the test (non-control) cocktails.

| VALVE | CONTROL | 12 µg | % CONTRL | 24 µg | % CONTRL | 48 µg | % CONTRL |
|---|---|---|---|---|---|---|---|
| B1163 | 3347 | 4516 | 135% | | | | |
| | 4927 | | | 3200 | 65% | | |
| | 2546 | | | | | 3602 | 141% |
| B1164 | 3557 | 3601 | 101% | | | | |
| | 3486 | | | 2169 | 62% | | |
| | 5031 | | | | | 4780 | 95% |
| B1165 | 3461 | 3789 | 109% | | | | |
| | 4014 | | | 2260 | 56% | | |
| | 3768 | | | | | 2944 | 78% |
| B1166 | 3569 | 1553 | 44% | | | | |
| | 3215 | | | 6539 | 203% | | |
| | 4012 | | | | | 6568 | 164% |
| B1168 | 2891 | 1565 | 54% | | | | |
| | 2193 | | | 1617 | 74% | | |
| | 2084 | | | | | 1316 | 63% |
| B1169 | 5202 | 3903 | 75% | | | | |
| | 3343 | | | 2775 | 83% | | |
| | 5030 | | | | | 4208 | 84% |
| AVG | | | 86% | | 90% | | 104% |

Example 4

Antibiotic cocktails containing the following antibiotics in the following concentrations were prepared and tested as described in Example 1.

| | |
|---|---|
| Imipenem | 12, 24, 48 or 96 µg/ml |
| Vancomycin | 50 µg/ml |
| Fluconazole | 100 µg/ml |

Paired valve leaflet halves were used. One half of each leaflet was used as a control and was treated with the antibiotic cocktail containing 12 µg/ml imipenem. The other half was treated with one of the test antibiotic cocktails containing 24, 48 or 96 µg/ml imipenem. The results of the assay for incorporation of $^3$-glycine into proteins are presented in the following table in DPM/mg and percent of control. The columns labeled 24, 48 and 96 µg indicate the amount of imipenem per ml used in the test antibiotic cocktails.

| VALVE | CONTROL | 24 µg | % CONTRL | 48 µg | % CONTRL | 96 µg | % CONTRL |
|---|---|---|---|---|---|---|---|
| B1178 | 1700 | 4458 | 262% | | | | |
| | 3267 | | | 1944 | 60% | | |
| | 2944 | | | | | 1907 | 65% |
| B1180 | 7227 | 9336 | 129% | | | | |
| | 11035 | | | 11321 | 103% | | |
| | 9493 | | | | | 12004 | 126% |

-continued

| VALVE | CONTROL | 24 µg | % CONTRL | 48 µg | % CONTRL | 96 µg | % CONTRL |
|---|---|---|---|---|---|---|---|
| B1181 | 3806 | 4802 | 126% | | | | |
| | 7091 | | | 4942 | 70% | | |
| | 3651 | | | | | 3322 | 91% |
| B1182 | 6375 | 6372 | 100% | | | | |
| | 6050 | | | 8826 | 146% | | |
| | 9135 | | | | | 6524 | 71% |
| B1184 | 6621 | 8093 | 122% | | | | |
| | 6219 | | | 9415 | 151% | | |
| | 7324 | | | | | 9272 | 127% |
| B1185 | 8312 | 5054 | 95% | | | | |
| | 6444 | | | 6755 | 105% | | |
| | 6422 | | | | | 5851 | 91% |
| AVERAGE | | | 139% | | 106% | | 90% |

Example 5

Antibiotic cocktails containing the following antibiotics in the following concentrations were prepared and tested as described in Example 1.

| | |
|---|---|
| Imipenem | 12 µg/ml |
| Vancomycin | 50 µg/ml |
| Fluconazole | 100 µg/ml |
| Rifampin | 10 µg/ml. |
| Amphotericin B | 0, 0.3, 1.0 or 3.0 µg/ml. |

The amphotericin B dilutions were made as follows. A bottle containing 50 mg amphotericin B (E.R. Squibb & Sons, Inc., Princeton, N.J.; trade name FUNGIZONE) was reconstituted with 10 ml of sterile water. One ml of this solution was removed and further diluted with 9 ml of Solution B to give a concentration of 500 µg/ml. Further dilutions were made from this stock solution in Solution B.

Paired valve leaflet halves were used. One half of each leaflet was a control and was treated with the antibiotic cocktail without any amphotericin B. The other half was treated with one of the test antibiotic cocktails containing amphotericin B. The results of the assay for incorporation of $^3$H-glycine into proteins are presented in the following table in DPM/mg and percent of control. In the table, the concentrations refer to the concentration of amphotericin B used in the test antibiotic cocktails.

A concentration of 0.3 µg/ml amphotericin B in the antibiotic mixture yielded tissue which has an average viability greater than the control. Tissue viability was reduced by 1 and 3 µg/ml of amphotericin B to 74% and 72% of control, respectively.

Example 6

Antibiotic cocktails containing the following antibiotics in the following concentrations were prepared and tested as described in Examples 1 and 5, except that the valve leaflet halves were only incubated in the antibiotic cocktails for 24 hours, instead of 48 hours.

| | |
|---|---|
| Imipenem | 48 µg/ml |
| Vancomycin | 50 µg/ml |
| Fluconazole | 100 µg/ml |
| Rifampin | 0, 10, 30 or 60 µg/ml |
| Amphotericin B | 0.3 µg/ml. |

Paired valve leaflet halves were used. One half of each leaflet was a control and was treated with the antibiotic cocktail without any rifampin. The other half was treated with one of the test antibiotic cocktails containing rifampin. The results of the assay for incorporation of $^3$-glycine into proteins are presented in the following table in DPM/mg and percent of control. In the table, the concentrations refer to the concentration of rifampin used in the test antibiotic cocktails.

| VALVE | CONTROL | 3 µg/ml | % CONTRL | 1 µg/ml | % CONTRL | 0.3 µg/ml | % CONTRL |
|---|---|---|---|---|---|---|---|
| B1170 | 6026 | 5799 | 96% | | | | |
| | 4401 | | | 3397 | 77% | | |
| | 7638 | | | | | 5281 | 69% |
| B1171 | 2428 | 470 | 19% | | | | |
| | 1666 | | | 619 | 37% | | |
| | 873 | | | | | 1692 | 194% |
| B1173 | 6729 | 5390 | 80% | | | | |
| | 8068 | | | 4619 | 57% | | |
| | 7206 | | | | | 8148 | 113% |
| B1174 | 5894 | 4694 | 80% | | | | |
| | 4841 | | | 4616 | 95% | | |
| | 4040 | | | | | 6724 | 166% |
| B1175 | 12453 | 7584 | 61% | | | | |
| | 6666 | | | 6130 | 92% | | |
| | 6482 | | | | | 6704 | 103% |
| B1177 | 6281 | 6182 | 98% | | | | |
| | 3682 | | | 3294 | 89% | | |
| | 2159 | | | | | 4074 | 189% |
| AVERAGE | | | 72% | | 74% | | 139% |

| VALVE | CONTROL | 10 µg/ml | % CONTRL | 30 µg/ml | % CONTRL | 60 µg/ml | % CONTRL |
|---|---|---|---|---|---|---|---|
| B1199 | 4098 | 2552 | 62% |  | 58% |  |  |
|  | 2311 |  |  | 1348 |  |  |  |
|  | 2846 |  |  |  |  | 2099 | 74% |
| B1200 | 1974 | 3512 | 178% |  |  |  |  |
|  | 1216 |  |  | 2279 | 187% |  |  |
|  | 2286 |  |  |  |  | 630 | 28% |
| B1202 | 2238 | 2704 | 121% |  |  |  |  |
|  | 2365 |  |  | 2310 | 98% |  |  |
|  | 3470 |  |  |  |  | 1805 | 52% |
| B1203 | 3540 | 3001 | 85% |  |  |  |  |
|  | 4239 |  |  | 4241 | 100% |  |  |
|  | 4035 |  |  |  |  | 2643 | 66% |
| B1204 | 3709 |  |  | 2640 | 64% |  |  |
|  | 3368 |  |  |  |  | 2025 | 56% |
| B1207 | 5970 | 4773 | 80% |  |  |  |  |
|  | 7433 |  |  | 3980 | 54% |  |  |
|  | 6174 |  |  |  |  | 3829 | 62% |
| B1209 | 6029 | 3597 | 60% |  |  |  |  |
|  | 2752 |  |  | 5750 | 209% |  |  |
|  | 3875 |  |  |  |  | 1487 | 38% |
| B1210 | 11545 | 5436 | 47% |  |  |  |  |
|  | 11317 |  |  | 7136 | 63% |  |  |
|  | 7415 |  |  |  |  | 6281 | 85% |
| B1211 | 5637 | 3180 | 56% |  |  |  |  |
|  | 6182 |  |  | 3336 | 54% |  |  |
|  | 7903 |  |  |  |  | 677 | 9% |
| B1213 | 5724 | 4597 | 80% |  |  |  |  |
|  | 8390 |  |  | 4418 | 53% |  |  |
|  | 4721 |  |  |  |  | 3879 | 82% |
| AVERAGE |  |  | 85% |  | 94% |  | 55% |

Example 7

An experiment was performed to compare $^3$H-glycine incorporation by fresh tissue with $^3$-glycine incorporation by tissue processed in various ways. All procedures were the same as those described in Examples 1 and 5, except as otherwise indicated below.

The three leaflets were removed from each of eight valves, and each leaflet was cut in half. The six leaflet halves were treated as follows:

| | |
|---|---|
| Leaflet 1A | Fresh control, no antibiotic treatment, no cryopreservation. |
| Leaflet 1B | Incubated with Solution B for 24 hours at 37° C. and cryopreserved. |
| Leaflet 2A | Fresh control, no antibiotic treatment, no cryopreservation. |
| Leaflet 2B | Incubated with antibiotic cocktail at 37° C. for 24 hours and cryopreserved. |
| Leaflet 3A | Incubated with Solution B for 24 hours at 37° C. and cryopreserved. |
| Leaflet 3B | Incubated with antibiotic cocktail at 37° C. for 24 hours and cryopreserved. |

All fresh control valve leaflet halves were immediately labeled with $^3$H-glycine and processed for scintillation counting. After thawing, the Solution B-treated and antibiotic-treated valve leaflet halves were also labeled with $^3$H-glycine and processed for scintillation counting.

The antibiotic cocktail consisted of:

| | |
|---|---|
| Imipenem | 48 µg/ml |
| Vancomycin | 50 µg/ml |
| Fluconazole | 100 µg/ml |
| Amphotericin B | 0.3 µg/ml |

The results are presented in the following table. The numbers are DPM/mg.

| VALVE | LEAFLET | FRESH | SOL. B | ANTIBIOTICS |
|---|---|---|---|---|
| B1222 | 1 | 5097 | 7110 |  |
|  | 2 | 4155 |  | 9311 |
|  | 3 |  | 6610 | 6439 |
| B1223 | 1 | 4684 | 9400 |  |
|  | 2 | 5582 |  | 8131 |
|  | 3 |  | 8364 | 6841 |
| B1226 | 1 | 3670 | 8153 |  |
|  | 2 | 3987 |  | 11425 |
|  | 3 |  | 7817 | 7757 |
| B1229 | 1 | 6107 | 8177 |  |
|  | 2 | 8470 |  | 9683 |
|  | 3 |  | 7945 | 6297 |
| B1230 | 1 | 6067 | 7412 |  |
|  | 2 | 4098 |  | 6935 |
|  | 3 |  | 4258 | 5523 |
| B1232 | 1 | 3022 | 5474 |  |
|  | 2 | 2534 |  | 7574 |
|  | 3 |  | 6138 | 4051 |
| B1233 | 1 | 2451 | 4436 |  |
|  | 2 | 3701 |  | 10861 |
|  | 3 |  | 6364 | 5402 |
| B1234 | 1 | 5666 | 2870 |  |
|  | 2 | 5006 |  | 3476 |
|  | 3 |  | 4185 | 3233 |
| MEAN |  | 4643 | 6545 | 7059 |
| STD DEV |  | 1544 | 1852 | 2450 |
| SEM |  | 386 | 463 | 612 |

There is a statistically significant difference between the fresh control group and the two groups incubated at 37° C. before cryopreservation. There is no statistical difference between the Solution B-treated and the antibiotic-treated groups. Statistical analysis was performed using the Student-Newman-Keuls method.

Example 8

Antibiotic cocktails containing the following antibiotics in the following concentrations were prepared and tested as described in Examples 1 and 5.

| | |
|---|---|
| Imipenem | 48, 72 or 96 µg/ml |
| Vancomycin | 50 µg/ml |
| Fluconazole | 100 µg/ml |
| Amphotericin B | 0.3 µg/ml. |

The three leaflets from each valve were cut in half. One half of each leaflet was incubated with an antibiotic cocktail containing a particular concentration of imipenem for 24 hours, and the other half was incubated with the same antibiotic cocktail for 48 hours as follows:

Leaflet 1A—48 µg/ml imipenem, 24 hours

1B—48 µg/ml imipenem, 48 hours

2A—72 µg/ml imipenem, 24 hours

2B—72 µg/ml imipenem, 48 hours

3A—96 µg/ml imipenem, 24 hours

3B—96 µg/ml imipenem, 48 hours

The results of the assay for incorporation of $^3$H-glycine into proteins are presented in the following table in DPM/mg. In the table, the concentrations refer to the concentration of imipenem used in the antibiotic cocktails.

| | 48 µg/ml | | 72 µg/ml | | 96 µg/ml | |
|---|---|---|---|---|---|---|
| Valve | 24 h | 48 h | 24 h | 48 h | 24 h | 48 h |
| B1245 | 7053 | 5875 | 9219 | 9933 | 4977 | 6236 |
| B1246 | 5526 | 5758 | 7670 | 6128 | 5375 | 5805 |
| B1247 | 3252 | 6582 | 6713 | 5808 | 7105 | 8708 |
| B1256 | 2643 | 3459 | 2796 | 2876 | 2677 | 2602 |
| B1257 | 3188 | 4685 | 5661 | 5724 | 5982 | 1792 |
| B1258 | 6322 | 4947 | 6503 | 7195 | 7025 | 12875 |
| B1259 | 9798 | 7731 | 14088 | 14544 | 7409 | 12861 |
| B1260 | 3700 | 3584 | 3214 | 5586 | 5053 | 4185 |
| B1266 | 3671 | 4887 | 4022 | 5273 | 4016 | 4551 |
| B1267 | 7535 | 5655 | 9086 | 8917 | 9233 | 5647 |
| MEAN | 5269 | 5316 | 6897 | 7198 | 5885 | 6526 |
| SEM | 748 | 411 | 1069 | 1026 | 595 | 1219 |

Statistical analysis of this data by the student's T-test shows that there is no statistical difference between any of the treatment groups.

Example 9

Antibiotic cocktails containing the following antibiotics in the following concentrations were prepared and tested as described in Examples 1 and 5, except that the valve leaflet halves were incubated in the antibiotic cocktails for 24 hours only.

| | |
|---|---|
| Imipenem | 96 µg/ml, |
| Vancomycin | 50 µg/ml, |
| Fluconazole | 100 µg/ml, | and one of the following:

| | |
|---|---|
| 0.3 µg/ml amphotericin B | Control |
| 0.6 µg/ml amphotericin B | I |
| 1.0 µg/ml amphotericin B | II |
| 0.6 µg/ml amphotericin B plus 50 µg/ml netilmicin | III |

The results of the assay for incorporation of $^3$H-glycine into proteins are presented in the following table units in DPM/mg). Note that valves B1307, B1310, and B1311 had an incorrect concentration of netilmicin added in the cocktail. These data were therefore not included.

| VALVE | CONTROL | I | II | III |
|---|---|---|---|---|
| B1307 | 4438 | 7264 | | |
| | 6370 | | 5770 | |
| B1310 | 1773 | 2522 | | |
| | 2107 | | 4091 | |
| B1311 | 2712 | 1617 | | |
| | 1560 | | 1495 | |
| B1313 | 3940 | 3790 | | |
| | 4644 | | 3058 | |
| | 2841 | | | 1598 |
| B1315 | 3678 | 3588 | | |
| | 4727 | | 4941 | |
| | 3570 | | | 4476 |
| B1316 | 7255 | 9624 | | |
| | 8867 | | 10954 | |
| | 5510 | | | 7924 |
| B1317 | 4039 | 4261 | | |
| | 7180 | | 5096 | |
| | 2703 | | | 3240 |
| B1318 | 5461 | 7025 | | |
| | 7704 | | 9013 | |
| | 7838 | | | 7346 |
| B1319 | 3178 | 3435 | | |
| | 2983 | | 2963 | |
| | 3190 | | | 2847 |
| B1320 | 9820 | 8535 | | |
| | 5527 | | 5256 | |
| | 7530 | | | 7866 |
| B1321 | 4528 | 2870 | | |
| | 5439 | | 4486 | |
| | 3872 | | | 3763 |
| B1322 | 3815 | 3544 | | |
| | 3511 | | 2269 | |
| | 4205 | | | 3249 |
| B1324 | 6268 | 7065 | | |
| | 4692 | | 4438 | |
| | 7847 | | | 6492 |
| B1325 | 4839 | 5273 | | |
| | 4516 | | 4462 | |
| | 5922 | | | 6478 |

| | Statistical analysis: | | |
|---|---|---|---|
| | Mean | Std. Dev | SEM |
| Control | 4887 | 1997 | 320 |
| 0.6 Amp B | 5030 | 2451 | 655 |
| 1.0 Amp B | 4878 | 2502 | 669 |
| .6 Amp B + Netil | 5025 | 2255 | 680 |

Using the Kruskal-Wallis one way anova on ranks, there is no statistical difference between the groups (P=0.994). Therefore, the antibiotic regimens tested provide tissue which is equally viable.

Example 10

Antibiotic cocktails were prepared and tested as described in Examples 1 and 5, except that the valve leaflet halves were incubated in the antibiotic cocktails for 24 hours only. Paired valve leaflet halves were used. One half of each leaflet was used as a control and treated with the following antibiotic cocktail:

| | |
|---|---|
| Imipenem | 96 µg/ml |
| Vancomycin | 50 µg/ml |
| Fluconazole | 100 µg/ml |
| Amphotericin B | 0.6 µg/ml. |

The other half was treated with one of the following test antibiotic cocktails:

| | |
|---|---|
| Imipenem | 96 µg/ml |
| Vancomycin | 50 µg/ml |
| Fluconazole | 100 µg/ml |
| Amphotericin B | 0.6 µg/ml |
| Netilmicin | 20, 30 or 50 µg/ml. |

The results of the assay for incorporation of $^3$H-glycine into proteins are presented in the following table in DPM/mg and percent of control. The columns labeled 20, 30 and 50 µg/ml indicate the concentration of netilmicin used in the test (non-control) cocktails.

| VALVE | CONTROL | 20 µg/ml | % contr | 30 µg/ml | % contr | 50 µg/ml | % contr |
|---|---|---|---|---|---|---|---|
| B1326 | 6762 | 4218 | 62% | | | | |
| | 5259 | | | 4944 | 94% | | |
| | 3701 | | | | | 4309 | 116% |
| B1327 | 4433 | 4506 | 102% | | | | |
| | 7519 | | | 9040 | 120% | | |
| | 6210 | | | | | 6714 | 108% |
| B1328 | 6504 | 4648 | 71% | | | | |
| | 6862 | | | 7312 | 107% | | |
| | 4225 | | | | | 3514 | 83% |
| B1329 | 4233 | 4193 | 99% | | | | |
| | 6058 | | | 6569 | 108% | | |
| | 5331 | | | | | 5188 | 97% |
| B1331 | 3646 | 3530 | 97% | | | | |
| | 3682 | | | 5611 | 152% | | |
| | 2988 | | | | | 4516 | 151% |
| B1332 | 3910 | 5831 | 149% | | | | |
| | 6968 | | | 6736 | 97% | | |
| | 7404 | | | | | 6046 | 82% |
| B1333 | 1327 | 1929 | 145% | | | | |
| | 1160 | | | 2660 | 229% | | |
| | 472 | | | | | 433 | 91% |
| B1334 | 7628 | 4994 | 65% | | | | |
| | 9000 | | | 10401 | 116% | | |
| | 8553 | | | | | 11484 | 134% |
| B1337 | 6624 | 5048 | 76% | | | | |
| | 6290 | | | 6440 | 102% | | |
| | 6766 | | | | | 6349 | 94% |
| B1338 | 2843 | 3233 | 114% | | | | |
| | 9114 | | | 8342 | 92% | | |
| | 4908 | | | | | 4218 | 86% |
| B1340 | values too low | | | | | | |
| AVG | 5514 | 4213 | 98% | 6805 | 122% | 5815 | 104% |

Example 11

Antibiotic cocktails were prepared and tested as described in Examples 1 and 5, except that the valve leaflet halves were incubated in the antibiotic cocktails for 24 hours only. Paired valve leaflet halves were used. One half of each leaflet was used as a control and treated with the following antibiotic cocktail:

| | |
|---|---|
| Imipenem | 96 µg/ml |
| Vancomycin | 50 µg/ml |
| Fluconazole | 100 µg/ml |
| Netilmicin | 50 µg/ml. |

The other half was treated with one of the following test antibiotic cocktails:

| | |
|---|---|
| Imipenem | 96 µg/ml |
| Vancomycin | 50 µg/ml |
| Fluconazole | 100 µg/ml |
| Netilmicin | 50 µg/ml |
| Amphotericin B | 0.3, 0.6, 1.0, 2.0 or 3.0 µg/ml. |

The results of the assay for incorporation of $^3$H-glycine into proteins are presented in the following table in DPM/mg. The results for the $^3$-hypoxanthine autoradiography are presented in the second table as percent live cells compared to total number of cells. The columns labeled 0.3, 0.6, 1.0, 2.0 or 3.0 µg/ml indicate the concentration of amphotericin B used in the test (non-control) cocktails.

| VALVE | CONTROL | 0.3 µg/ml | 0.6 µg/ml | 1.0 µg/ml | 2.0 µg/ml | 3.0 µg/ml |
|---|---|---|---|---|---|---|
| B1341 | 3658 | 4388 | 4643 | 4937 | 4248 | 2569 |
| B1342 | 6198 | 4655 | | | 2795 | 3218 |

-continued

| VALVE | CONTROL | 0.3 µg/ml | 0.6 µg/ml | 1.0 µg/ml | 2.0 µg/ml | 3.0 µg/ml |
|---|---|---|---|---|---|---|
| B1343 | 4293 | 3368 | 4450 | 4777 | 2744 | 2937 |
| B1347 | 4302 | 4938 | 4238 | 5127 | 3744 | 3443 |
| B1348 | 4488 | 5632 | 5979 | 5136 | 5804 | 3653 |
| B1349 | 8769 | 8540 | 7646 | 4377 | 8094 | 6033 |
| B1351 | 5806 | 5413 | 7156 | 5833 | 3498 | 5743 |
| B1352 | 7242 | 5254 | 3777 | 4888 | 3921 | 5177 |
| B1353 | 3740 | 4147 | 3291 | 3657 | 2964 | 3212 |
| B1355 | 1813 | 1064 | 1565 | 2083 | 1923 | 2028 |
| B1358 | 4974 | 6902 | 4854 | 5284 | 6209 | 7139 |
| B1360 | 3388 | 3319 | 2796 | 2448 | 2945 | 2867 |
| B1361 | 10903 | 7264 | 6773 | 7783 | 6793 | 9171 |
| B1363 | 7340 | 4628 | 7321 | 7463 | 3620 | 5134 |
| MEAN | 5494 | 4965 | 4960 | 4914 | 4236 | 4452 |
| SEM | 645 | 493 | 526 | 452 | 480 | 543 |
| avg % control |  | 90% | 90% | 89% | 77% | 81% |

| VALVE | CONTROL | 0.3 µg/ml | 0.6 µg/ml | 1.0 µg/ml | 2.0 µg/ml | 3.0 µg/ml |
|---|---|---|---|---|---|---|
| B1350 | 76.5% | 75.7% | 67.5% | 69% | 70.5% | 76.5% |
| B1354 | 82% | 61.5% | 82.8% | 76.3% | 68.3% | 75.3% |
| B1356 | 81% | 86% | 84% | 64% | 68% | 55.5% |
| B1359 | 91% | 58% | 66% | 59% | 71% | 70% |
| MEAN | 82.6% | 70.3% | 75.1% | 67.1% | 69.5% | 69.3% |
| avg % control |  | 85% | 91% | 81% | 84% | 84% |

Example 12

An experiment was performed to determine the viability of valve leaflets processed using Cocktail C, Cocktail D or Cocktail B plus Cocktail C. See Example 1 for the formulations of Cocktails B and C. Cocktail D has the following formulation:

| Imipenem | 96 µg/ml |
|---|---|
| Vancomycin | 50 µg/ml |
| Fluconazole | 100 µg/ml |
| Amphotericin B | 0.3 µg/ml. |

Unless otherwise specified; the cocktails were prepared and tested as described in Examples 1 and 5.

Eleven human valves were used. One leaflet from each valve was incubated with Cocktail D for 24 hours (Method G). Another leaflet was incubated in Cocktail C for 24 hours (Method D) or in Cocktail C for 24 hours followed by incubation in Cocktail B for 24 hours (Method E). After thawing, each leaflet was cut in half. One half was labelled with $^3$-glycine, and the other half was labelled with $^3$-hypoxanthine. The results for the incorporation of $^3$H-glycine into protein are presented in the following table (units of DPM/mg).

| VALVE | Method | Method D/E | Method G |
|---|---|---|---|
| B1272 | D | 2008 | 1576 |
| B1274 | D | 1484 | 3858 |
| B1276 | D | 2527 | 2110 |
| B1277 | D | 3578 | 8432 |
| MEAN |  | 2399 | 3994 |
| SD |  | 894 | 3115 |
| B1273 | E | 742 | 2012 |
| B1275 | E | 4449 | 6267 |
| B1278 | E | 2317 | 2383 |
| B1279 | E | 388 | 410 |
| B1280 | E | 842 | 1047 |
| B1281 | E | 589 | 2122 |
| B1282 | E | 470 | 1326 |
| MEAN |  | 1400 | 2224 |
| SD |  | 1496 | 1911 |

Thus, treatment with Cocktail D containing antifungal agents fluconazole and amphotericin B (Method G) resulted in viability of valve leaflets comparable to or better than treatment with Cocktails B and C not containing antifungal agents (Methods D and E).

Example 13

An experiment was performed to compare the viability of heart valve tissue processed in one of the following ways:

Method F: Tissue with longer ischemic time (potentially lower cell viability) which was incubated with Cocktail C for 24 hours, optionally followed by incubation for 24 hours with Cocktail B (formulations given in Example 1). The decision to treat tissue with Cocktail B was made based on the results of microbiological cultures of tissue taken prior to antibiotic treatment with Cocktail C as described in McNally and Brockbank, *J. Med. Engineer. & Technol.*, 16, 34–38 (1992) and PCT application WO 92/12631.

Method H: Incubation with the following antibiotic cocktail, which will be designated Cocktail E, for 24 hours:

| Imipenem | 94–100 µg/ml |
|---|---|
| Vancomycin | 50 µg/ml |
| Netilmicin | 50 µg/ml |
| Fluconazole | 100 µg/ml |
| Amphotericin B | 1.0 µg/ml |

Cocktails B, C and E were prepared and tested as described in Examples 1 and 5, except as otherwise provided herein.

One leaflet was removed from each valve at dissection and cut in half. One half was immediately labeled with ³H-glycine, and the other half was immediately labeled with ³-hypoxanthine. These were the fresh controls.

The remainder of the valve was cut in half with one whole leaflet left intact in each half. One of the valve halves was treated by Method F (Cocktail C, optionally followed by treatment with Cocktail B). The other valve half was treated by Method H (Cocktail E). The frozen valve halves were thawed and cut in half. One half was labeled with ³-glycine, and one half was labeled ³-hypoxanthine.

The results are presented in the following table (units of DPM/mg for ³H-glycine incorporation into proteins and units of percent live cells compared to total cells for ³-hypoxanthine autoradiography).

Comparisons between treatment groups were made with the nonparametric Mann-Whitney rank sum test. When ³H-glycine was used to label the tissue there was no significant difference between the treatments (P=0.655). Likewise, when ³-hypoxanthine was used to label the tissue there was no significant difference between the two treated groups (P=0.684). Using the Kruskal-Wallis one way anova on ranks there was no significant difference between any of the 3 groups when ³H-glycine was used.

suspension). Serial dilutions were made as follows: (1) 0.5 ml of the 0.5 MacFarland turbidity standard was added to 4.5 ml of sterile normal saline (Tube A; expected population $10^5$ cfu/ml); (2) 0.1 ml of the Tube A suspension was added to 9.9 ml of sterile normal saline (Tube B; expected population $10^3$ cfu/ml); and (3) 0.1 ml of the Tube B suspension was added to 9.9 ml of sterile normal saline (Tube C; expected population 10 cfu/ml). Each serial dilution was vortexed for 30 seconds before the next transfer.

Solutions of fluconazole and amphotericin B having the concentrations given in the following table were made in Solution B.

| Cocktail | Fluconazole | Amphotericin B |
| --- | --- | --- |
| Control | 0 | 0 |
| I | 100 µg/ml | 0 |
| II | 100 µg/ml | 0.3 µg/ml |
| III | 0 | 0.6 µg/ml |

Tubes B and C were challenged with these cocktails. Each cocktail (24.0 ml) was placed into a sterile 115 ml plastic cup, and 1.0 ml of the yeast population from Tube B or C was added. The cups were mixed gently, capped and placed in the incubator for 24 hours at 35° C. After the prescribed

| VALVE | GLYCINE FRESH | HYPOXAN FRESH | GLYCINE METHOD F | HYPOXAN METHOD F | GLYCINE METHOD H | HYPOXAN METHOD H |
| --- | --- | --- | --- | --- | --- | --- |
| B1385 | 10557 | 70% | 2137 | 43% | 4802 | 52.6% |
| B1386 | 4120 | 75.8% | 2719 | 32% | 6742 | 61% |
| B1387 | 2493 | 72.3% | 2385 | 41.5% | 3645 | 41.4% |
| B1388 | 3366 | 41.2% | 3547 | 31.2% | 946 | 10.3% |
| B1389 | 6569 | 60.6% | 2066 | 30.6% | 1111 | 18.4% |
| B1390 | 2474 | 48.2% | 3253 | 26.8% | 5848 | 22.8% |
| B1391 | 2451 | 86.5% | 1420 | 26.3% | 2942 | 52% |
| B1392a | 1236 | 52.5% | 658 | 12.3% | 381 | 5.8% |
| B1392b | ND* | ND | 3196 | 39.8% | 5937 | 38.8% |
| B1393 | 5774 | 78.2% | 2798 | 31.4% | 4286 | 44.2% |
| B1394 | 3544 | 63.2% | 5840 | 42.4% | 6798 | 49.6% |
| B1395 | 4676 | 84.4% | 18298 | 55.3% | 13986 | 37.2% |
| B1396 | 4792 | 60.9% | 2778 | 27.4% | 2119 | 32.2% |
| B1397 | 4524 | 85.6% | 3639 | 39.8% | 3825 | 30.8% |
| B1399 | 4209 | 75.9% | 1698 | 10.9% | 1819 | 22.9% |
| B1400 | 3179 | 56% | 1533 | 29.8% | 9316 | 16.4% |
| B1401 | 3181 | 33.3% | 2402 | 30.2% | 2317 | 13.2% |
| B1402 | 1962 | 88.4% | 1716 | 18.5% | 2889 | 39.4% |
| B1403 | 1167 | 36.4% | 1730 | 54.7% | 1289 | 51.0% |
| B1406 | 2504 | 43.6% | 9662 | 43.6% | 2978 | 21.8% |
| B1407 | 3160 | 82.9% | 3816 | 28.3% | 2884 | 28.2% |
| B1408 | 11194 | 79.4% | 11264 | 40.0% | 7406 | 70.9% |
| B1409 | 896 | 81.6% | 4665 | 46.4% | 1822** | 59.6% |
| B1410 | 2044 | 68.6% | 7453 | 51.3% | 3804 | 44.4% |
| B1412 | 4248 | 21.8% | 2038 | 29.0% | 1652 | 50.0% |
| MEAN | 4062 | 64.5% | 4085 | 34.5% | 4155 | 36.6% |
| SD | 2535 | 19.1% | 3991 | 11.6% | 3104 | 17.3% |
| SEM | 529 | 3.9% | 815 | 2.3% | 634 | 3.5% |

*ND = not done
**very heavy plaque

Example 14

The *Candida albicans* used in these studies was ATCC strain 14053 (American Type Culture Collection). The purity of the strain was verified before and after cultivation.

The test organism was cultured on a Sabouraud Agar Plate, streaked for isolation, and incubated at 35° C. for 24 hours. A single colony was removed using a sterile cotton swab and placed in 5.0 ml of sterile saline. The mixture was vortexed, and dilutions were made and compared to a standard turbidity chart until the turbidity matched a 0.5 turbidity standard (a 0.5 MacFarland turbidity standard incubation period, 1.0 ml of the yeast-cocktail mixture was removed from each tube and processed to obtain an enumeration of the surviving yeast organisms. The remaining mixture was placed back into the incubator and incubated for an additional 24 hours. After this incubation period, the cups were removed, swirled gently and 1.0 ml was removed, and the above process was repeated.

Enumeration of the yeast was performed as follows; each sample was tested in duplicate. One milliliter (1.0 ml) of year suspension was added to the top assembly of a sterile disposable filter apparatus which contained 99 ml of sterile normal saline. The contents were mixed gently and filtered.

The filter pad was removed aseptically using sterile disposable forceps and placed on Sabouraud Agar plates. The plates were incubated at 35° C. for 24 hours, and the colonies were then counted.

The results are presented in the following tables. Tube B contained 734 colony forming units (CFU) of *C. albicans*/ml at time zero, and Tube C contained 13 cfu/ml at time zero.

| Tube B | 24 hr | 48 hr |
|---|---|---|
| I | 31 colonies | 45 colonies |
| II | 0 colonies | 0 |
| III | 0 colonies | 0 |

| Tube C | 24 hr | 48 hr |
|---|---|---|
| I | 0 colonies | 1 colony |
| II | 0 colonies | 0 colonies |
| III | 0 colonies | 0 colonies |

The results for Tube B show that 100 µg/ml fluconazole was effective in reducing the *C. albicans* bioburden from 734 colonies to 31 colonies at 24 hours. At 48 hours the colony count (45) suggests a tolerance or static phenomenon. Amphotericin B at 0.6 µg/ml and the combination of 100 µg/ml fluconazole and 0.3 µg/ml amphotericin B were fungicidal.

Example 15

The following antibiotic cocktails were prepared as described in Examples 1 and 5 and tested against ten yeast isolates:

| Cocktail | Content |
|---|---|
| I | Imipenem - 50 µg/ml<br>Vancomycin - 50 µg/ml<br>Fluconazole - 100 µg/ml<br>Amphotericin B - 0.3 µg/ml |
| II | Imipenem - 50 µg/ml<br>Vancomycin - 50 µg/ml<br>Fluconazole - 100 µg/ml<br>Amphotericin B - 0.6 µg/ml |
| III | Imipenem - 50 µg/ml<br>Vancomycin - 50 µg/ml<br>Fluconazole - 100 µg/ml<br>Amphotericin B - 1.0 µg/ml |
| IV | Imipenem - 50 µg/ml |

| Cocktail | Content |
|---|---|
| V | Vancomycin - 50 µg/ml<br>Amphotericin B - 0.3 µg/ml<br>Imipenem - 50 µg/ml<br>Vancomycin - 50 µg/ml<br>Amphotericin B - 0.6 µg/ml |
| VI | Imipenem - 50 µg/ml<br>Vancomycin - 50 µg/ml<br>Amphotericin B - 1.0 µg/ml |

The ten yeast isolates used were chosen because they are considered to be clinically significant human yeast isolates. The ten yeast isolates tested were:

1. *Rhodotorula rubra**
2. *Candida lusitaniae**
3. *Saccharomyces cervisae**
4. *Cryptococcus laurentii**
5. *Candida guilliermondii**
6. *Torulopsis glabrata**
7. *Candida tropicalis**
8. *Candida albicans*@
9. *Trichosporon beigeli*,
10. *Candida parasilosis**

* Provided by the American College of Pathologists.
@ The *Candida albican* isolate was obtained from donor tissue in which the yeast isolate had survived an antibacterial cocktail incubation. Identification was confirmed by using the Germ Tube Test for the confirmation of *Candida albicans*. The Germ Tube Test involves making a suspension of an isolate in a commercially prepared solution of bovine serum (REMEL). The mixture is incubated for 2–4 hour at 35° C. and examined microscopically. Confirmation of a positive germ tube is the formation of pseudohyphae budding (germination) off of the yeast bud cell.

The antibiotic cocktails were challenged with ten individual predetermined bioburden yeast suspensions as described in the previous example. The Sabouraud Agar plates were incubated at 35° C. for 5 days before enumeration and checked again at day 7 for any additional growth of yeast colonies. The 5 to 7 day incubation/enumeration period was chosen to provide the optimum recovery of any surviving yeast isolates which may grow after recovery from injury due to the presence of antifungal agents.

The results are presented in the following tables. Cocktail III exhibited the greatest fungicidal activity on all yeast isolates.

RESULTS WITH YEAST ISOLATES AT 24 HOURS (CFU/ml)

| Yeast isolate | Initial Bioburden | Positive Control | Cocktail I | Cocktail II | Cocktail III | Cocktail IV | Cocktail V | Cocktail VI |
|---|---|---|---|---|---|---|---|---|
| Rhodo. rubra | $1.2 \times 10^4$ | $6.2 \times 10^4$ | 460 | 106 | 10 | 469 | 140 | 10 |
| Candida luistan | $4.3 \times 10^4$ | $1.7 \times 10^5$ | 440 | 70 | 59 | 801 | 736 | 233 |
| Sacchar cervis | $1.8 \times 10^4$ | $9.4 \times 10^4$ | 530 | 151 | 11 | 155 | 15 | 12 |
| Crypto. lauren | NG | N/A | N/A | N/A | N/A | N/A | N/A | N/A |
| Candida guillie | $5.8 \times 10^4$ | $2.1 \times 10^5$ | 401 | 9 | 10 | 300 | 70 | 0 |
| Torulop glabra. | $3.7 \times 10^4$ | $2.0 \times 10^6$ | 20 | 0 | 0 | 10 | 0 | 0 |
| Candida tropica | $3.1 \times 10^4$ | $4.7 \times 10^6$ | 860 | 337 | 40 | 610 | 301 | 110 |
| Candida albican | $2.0 \times 10^4$ | $3.9 \times 10^6$ | 263 | 22 | 10 | 120 | 10 | 10 |
| Tricho beigeii | $1.1 \times 10^4$ | $4.1 \times 10^4$ | 0 | 0 | 0 | 810 | 167 | 154 |
| Candida parapsi | $2.8 \times 10^4$ | $8.7 \times 10^4$ | 20 | 13 | 0 | 510 | 380 | 170 |

| Yeast isolate | Initial Bio-burden | Positive control | Cocktail I | Cocktail II | Cocktail III | Cocktail IV | Cocktail V | Cocktail VI |
|---|---|---|---|---|---|---|---|---|
| *Rhodo. rubra* | $1.2 \times 10^4$ | $8.6 \times 10^5$ | 706 | 2150 | 388 | 4108 | 2100 | 660 |
| *Candida luistan* | $4.3 \times 10^4$ | $1.1 \times 10^9$ | 1180 | 1076 | 245 | 1978 | 1190 | 1011 |
| *Sacchar cervis* | $1.8 \times 10^4$ | $1.2 \times 10^5$ | 150 | 40 | 16 | 5010 | 87 | 0 |
| *Crypto. lauren* | NG | N/A | N/A | N/A | N/A | N/A | N/A | N/A |
| *Candida guillie* | $5.8 \times 10^4$ | $1.3 \times 10^8$ | 860 | 466 | 11 | 1987 | 454 | 71 |
| *Torulop glabra.* | $3.7 \times 10^4$ | $2.0 \times 10^7$ | 20 | 0 | 0 | 560 | 0 | 0 |
| *Candida tropica* | $3.1 \times 10^4$ | $1.7 \times 10^9$ | 2130 | 1208 | 528 | 1817 | 869 | 105 |
| *Candida albican* | $2.0 \times 10^4$ | $1.2 \times 10^7$ | 370 | 26 | 13 | 3640 | 2019 | 49 |
| *Tricho beigeii* | $1.1 \times 10^4$ | $2.3 \times 10^5$ | 0 | 0 | 0 | 9466 | 2019 | 610 |
| *Candida parapsi* | $2.8 \times 10^4$ | $3.6 \times 10^7$ | 56 | 33 | 15 | 1006 | 380 | 177 |

RESULTS WITH YEAST ISOLATES AT 48 HOURS (CFU/ml)

Comparison of Cocktail I (0.3 µg Amphotericin B) after 24 and 48 hours.

| YEAST ISOLATES | COCKTAIL I-24 hr | COCKTAIL I-48 hr | Net result |
|---|---|---|---|
| *Rhodoturla rubra* | 460 cfu/ml | 706 cfu/ml | 0 |
| *Candida lusitaniae* | 440 cfu/ml | 1180 cfu/ml | −1 |
| *Saccharomyces cervis* | 530 cfu/ml | 150 cfu/ml | +1 |
| *Cryptococcus laurenti* | NG | NG | NA |
| *Candida guilliermondii* | 401 cfu/ml | 860 cfu/ml | 0 |
| *Troulopsis glabrata* | 20 cfu/ml | 20 cfu/ml | 0 |
| *Candida tropicalis* | 860 cfu/ml | 2130 cfu/ml | −1 |
| *Candida albicans* | 263 cfu/ml | 370 cfu/ml | 0 |
| *Trichosporon beigeli* | 0 cfu/ml | 0 cfu/ml | 0 |
| *Candida parasilosis* | 20 cfu/ml | 56 cfu/ml | 0 |

A comparison of Cocktail I after 24 hours with Cocktail I after 48 hours indicates the usual tolerance phenomenon for yeast.

Comparison of Cocktails I and IV (0.3 µg amphotericin B with and without fluconazole) after 24 hours

| YEAST ISOLATES | COCKTAIL I | COCKTAIL IV | Net result |
|---|---|---|---|
| *Rhodoturla rubra* | 460 cfu/ml | 469 cfu/ml | 0 |
| *Candida lusitaniae* | 440 cfu/ml | 801 cfu/ml | −1 |
| *Saccharomyces cervis* | 530 cfu/ml | 155 cfu/ml | +1 |
| *Cryptococcus laurenti* | NG | NG | NA |
| *Candida guilliermondii* | 401 cfu/ml | 300 cfu/ml | 0 |
| *Troulopsis glabrata* | 20 cfu/ml | 10 cfu/ml | 0 |
| *Candida tropicalis* | 860 cfu/ml | 610 cfu/ml | 0 |
| *Candida albicans* | 263 cfu/ml | 120 cfu/ml | 0 |
| *Trichosporon beigeli* | 0 cfu/ml | 810 cfu/ml | −1 |
| *Candida parasilosis* | 20 cfu/ml | 510 cfu/ml | −1 |

Cocktail IV without fluconazole was not as effective as Cocktail I with fluconazole after 24 hours. The data indicate that the two antifungal agents give synergistic results when used together. See also the previous example.

Comparison of Cocktails II and V (0.6 µg amphotericin B with and without fluconazole) after 24 hours

| YEAST ISOLATES | COCKTAIL II | COCKTAIL V | Net result |
|---|---|---|---|
| *Rhodoturla rubra* | 106 cfu/ml | 140 cfu/ml | 0 |
| *Candida lusitaniae* | 70 cfu/ml | 736 cfu/ml | −1 |
| *Saccharomyces cervis* | 151 cfu/ml | 15 cfu/ml | +1 |
| *Cryptococcus laurenti* | NG | NG | NA |
| *Candida guilliermondii* | 9 cfu/ml | 70 cfu/ml | 0 |
| *Troulopsis glabrata* | 0 cfu/ml | 0 cfu/ml | 0 |
| *Candida tropicalis* | 337 cfu/ml | 301 cfu/ml | 0 |
| *Candida albicans* | 22 cfu/ml | 10 cfu/ml | 0 |
| *Trichosporon beigeli* | 0 cfu/ml | 167 cfu/ml | −1 |
| *Candida parasilosis* | 13 cfu/ml | 380 cfu/ml | −1 |

Cocktail V without fluconazole was not as effective as Cocktail II with fluconazole after 24 hours. The data indicate that the two antifungal agents give synergistic results when used together. See also the previous example.

Comparison of Cocktails III and VI (1.0 µg Amphotericin B with and without fluconazole) after 24 hours

| YEAST ISOLATES | COCKTAIL III | COCKTAIL VI | Net result |
|---|---|---|---|
| *Rhodoturla rubra* | 10 cfu/ml | 10 cfu/ml | 0 |
| *Candida lusitaniae* | 59 cfu/ml | 233 cfu/ml | −1 |
| *Saccharomyces cervis* | 11 cfu/ml | 12 cfu/ml | 0 |
| *Cryptococcus laurenti* | NG | NG | NA |
| *Candida guilliermondii* | 11 cfu/ml | 0 cfu/ml | 0 |
| *Troulopsis glabrata* | 0 cfu/ml | 0 cfu/ml | 0 |
| *Candida tropicalis* | 40 cfu/ml | 110 cfu/ml | 0 |

-continued

Comparison of Cocktails III and VI
(1.0 μg Amphotericin B with and without
fluconazole) after 24 hours

| YEAST ISOLATES | COCKTAIL III | COCKTAIL VI | Net result |
|---|---|---|---|
| Candida albicans | 10 cfu/ml | 10 cfu/ml | 0 |
| Trichosporon beigeli | 0 cfu/ml | 154 cfu/ml | −1 |
| Candida parasilosis | 0 cfu/ml | 170 cfu/ml | −1 |

Cocktail VI without fluconazole was not as effective as Cocktail III with fluconazole after 24 hours. The data indicate that the two antifungal agents gave synergistic results when used together. See also the previous example.

Example 16

Example 15 was repeated using the following antibiotic cocktails:

| Cocktail | Content |
|---|---|
| I | Imipenem - 50 μg/ml |
|   | Vancomycin - 50 μg/ml |
|   | Fluconazole - 100 μg/ml |
|   | Amphotericin B - 0.3 μg/ml |
| VII | Imipenem - 50 μg/ml |
|   | Vancomycin - 50 μg/ml |
|   | Netilmicin - 50 μg/ml |
|   | Fluconazole - 50 μg/ml |
|   | Amphotericin B - 1.0 μg/ml |
| VIII | Imipenem - 50 μg/ml |
|   | Vancomycin - 50 μg/ml |
|   | Netilmicin - 50 μg/ml |
|   | Fluconazole - 100 μg/ml |
|   | Amphotericin B - 1.0 μg/ml |

Ten different yeast isolates were used. These organisms were chosen because they had been recovered from cardiovascular donor tissue. They were:

11. *Candida albicans*
12. *Candida albicans*
13. *Candida albicans*
14. *Candida albicans*
15. *Candida albicans*
16. Yeast, not *Candida albicans*
17. Yeast, not *Candida albicans*
18. *Candida albicans*
19. Yeast, not *Candida albicans*
20. Yeast, not *Candida albicans*

Identification was made using the Germ Tube Test. The results after 24 hours of incubation in the antibiotic cocktails are presented in the following table (units are CFU/ml).

| Ten yeast Isolates recovered from donor tissue | Initial Yeast Bio-burden | Control at 24 hours | Cocktail I | Cocktail VII | Cocktail VIII |
|---|---|---|---|---|---|
| Candida albicans | $1.6 \times 10^3$ | $2.6 \times 10^4$ | 700 cfu | 0 cfu | 0 cfu |
| Candida albicans | $1.2 \times 10^3$ | $6.3 \times 10^4$ | 886 cfu | 10 cfu | 0 cfu |
| Candida albicans | $1.8 \times 10^4$ | $6.8 \times 10^4$ | 501 cfu | 0 cfu | 0 cfu |
| Candida albicans | $3.9 \times 10^3$ | $1.6 \times 10^4$ | 921 cfu | 0 cfu | 0 cfu |
| Candida albicans | $1.3 \times 10^3$ | $8.1 \times 10^3$ | 586 cfu | 0 cfu | 0 cfu |
| Yeast, not C. alb. | $4.8 \times 10^3$ | $2.7 \times 10^4$ | 70 cfu | 0 cfu | 0 cfu |
| Yeast, not C. alb. | $7.0 \times 10^3$ | $4.6 \times 10^4$ | 47 cfu | 0 cfu | 0 cfu |
| Candida albicans | $1.6 \times 10^3$ | $7.3 \times 10^3$ | 320 cfu | 40 cfu | 0 cfu |
| Yeast, not C. alb. | $9.8 \times 10^2$ | $2.3 \times 10^3$ | 689 cfu | 0 cfu | 0 cfu |
| Yeast, not C. alb. | $5.9 \times 10^3$ | $3.3 \times 10^4$ | $1.1 \times 10^3$ | 0 cfu | 0 cfu |

The addition of netilmicin at 50 μg/ml (Cocktails VII and VIII) did not have any adverse effects on the fungicidal activity of fluoconazole and amphotericin B. The increase of amphotericin B from 0.3 μg/ml (Cocktail I) to 1.0 μg/m (Cocktails VII and VIII) shows greater fungicidal activity. The reduction of fluconazole from 100 μg/ml to 50 μg/ml in the presence of 1.0 μg/ml amphotericin B (Cocktail VII versus Cocktail VIII) did not affect the fungicidal activity greatly.

Example 17

Heart valves from 223 donors were dissected as described in U.S. Pat. No. 4,890,457. The dissected valves were decontaminated using one of the methods listed below.

Duplicate sets of specimens consisting of approximately one gram of tissue were prepared at dissection. One set of specimens was treated by prior art processing method D, E, or F (described in Examples 12 and 13). The remaining set of samples was treated using a single antibiotic mixture, Cocktail E according to the invention.

| METHOD | ANTIBIOTIC COCKTAIL | TIME/TEMPERATURE |
|---|---|---|
| D | C | 22–26 Hr/37° C. |
|   | 12 μg/ml imipenem |   |
|   | 50 μg/ml vancomycin |   |
| E | C | 22–26 Hr/37° C. |
|   | 12 μg/ml imipinem |   |
|   | 50 μg/ml vancomycin |   |
|   | + |   |
|   | B | 22/26 Hr/37° C. |
|   | 62 μg/ml rifampin |   |
|   | 57 μg/ml netilmicin |   |
|   | 114 μg/ml vancomycin |   |
|   | 136 μg/ml cefotaxime |   |
|   | 136 μg/ml lincomycin |   |
| F | C | 22–26 Hr/37° C. |
|   | 12 μg/ml imipenem |   |
|   | 50 μg/ml vancomycin |   |
|   | + optionally |   |
|   | B | 22–26 Hr/37° C. |
|   | 62 μg/ml rifampin |   |
|   | 57 μg/ml netilmicin |   |
|   | 114 μg/ml vancomycin |   |
|   | 136 μg/ml cefotaxime |   |
|   | 136 μg/ml lincomycin |   |
| H | E | 22–26 Hr/37° C. |
|   | 94–100 μg/ml imipenem |   |

| METHOD | ANTIBIOTIC COCKTAIL | TIME/TEMPERATURE |
|--------|---------------------|------------------|
|        | 50 µg/ml vancomycin |                  |
|        | 57 µg/ml netilmicin |                  |
|        | 100 µg/ml fluconazole |                |
|        | 1.0 µg/ml amphotericin B |             |

Microbiological analyses were performed as follows. For each dissected heart, three sets of tissue samples were prepared at dissection to represent the product prior to treatment with antibiotics (pretreatment) and subsequent to antibiotic treatment (post treatment). The samples taken were pieces of external heart muscle tissue, pieces of the mitral or tricuspid valve, pieces of muscle tissue proximal to the aortic or pulmonary valve, and several milliliters of solution in which the heart was received.

After dissection, the pretreatment set of samples was submitted to the microbiology laboratory for microbial analysis of organisms present. Of the remaining duplicate sets of specimens one was treated along with the heart valves by the method D, E or F. The other set was treated by method Z.

At the end of each treatment period the specimens were aseptically collected and sent to the microbiology lab for analysis. Each set of specimens was assayed separately.

Tissue samples were homogenized by pouring the sample into a sterile plastic bag and placing into a stomacher for 30–60 seconds. The homogenized tissue samples were cultured on the following media: blood agar plate; chocolate agar plate; blood agar plate (anaerobic); enriched thioglycollate broth; Sabouraud's agar with gentamicin; and Sabouraud's heart infusion agar with blood.

Both the blood agar and the chocolate agar plates were incubated in 5–10% $CO_2$ in air at 35° C. for 4 days and observed on the 2nd and 4th days. The thioglycollate broth tubes were incubated at 35° C. for 14 days and observed daily for the first 7 days and periodically thereafter. The Sabouraud's agar plates were incubated at 30° C., and the plates were observed 2 times each the first week and again at 14 days.

The cultures were observed visually for growth. Gram stains were prepared of all positive cultures and of any negative thioglycollate broths to confirm "negative" visual observations. Accepted state-of-the-art microbiological tests were utilized to identify positive cultures.

The results of the microbiological analyses were presented below:

| METHOD D vs. METHOD H | | |
|---|---|---|
| 134 Heart Donors | Method D | No growth on 132; Propionibacterium acnes isolated on 2; 98% effective |
|  | Method H | No growth on 134; 100% effective |
| METHOD E vs. METHOD H | | |
| 64 Heart Donors | Method E | No growth on 60; Yeast isolated on 4; 94% effective |
|  | Method H | No growth on 64; 100% effective |
| METHOD F vs. METHOD H | | |
| 24 Heart Donors | Method F | No growth on 23; Group B streptococcus and Enterobacter species isolated on 1. 96% effective |
|  | Method H | No growth on 24; 100% effective |
| CUMULATIVE RESULTS: | | |
| Methods D, E, F | | Method H |
| 216 No growth, 97% effective 7 Growth | | 223 No growth, 100% effective |

No bacterial or fungal growth was observed in any Method H specimens. Thus, Cocktail E is superior to Cocktails B and C (used singly or in combination in Methods D, E and F) in inhibiting bacterial growth, as well as growth of yeast. No bacterial or fungal growth was observed in any Method H specimens. Thus, Cocktail E is superior to Cocktails B and C (used singly or in combination in Methods D, E and F) in inhibiting bacterial growth, as well as growth of yeast.

It is intended that the foregoing detailed description be regarded as illustrative, rather than limiting, and that it be understood that it is the following claims, including all equivalents, which are intended to define the scope of this invention.

We claim:

1. An antibiotic cocktail for decontaminating tissue for transplantation comprising:

amphotericin B and fluconazole as antifungal agents; and
   a plurality of antibacterial agents;
   the agents being present in amounts effective to substantially inhibit yeast and bacterial growth while substantially maintaining the viability of the tissue.

2. The antibiotic cocktail of claim 1 wherein the antibacterial agents comprise vancomycin and imipenem.

3. The antibiotic cocktail of claim 2 wherein the antibacterial agents further comprise netilmicin.

4. The antibiotic cocktail of claim 1 wherein the amphotericin B is present at a concentration of from about 0.3 µg per milliliter to about 2.0 µg per milliliter and the fluconazole is present at a concentration of from about 50 µg per milliliter to about 100 µg per milliliter.

5. The antibiotic cocktail of claim 4 wherein the antibacterial agents comprise vancomycin and imipenem.

6. The antibiotic cocktail of claim 5 wherein the vancomycin is present at a concentration of about 50 µg per milliliter and the imipenem is present at a concentration of about 10–100 µg per milliliter.

7. The antibiotic cocktail of claim 6 wherein the amphotericin B is present at a concentration of 0.3 µg per milliliter, the fluconazole is present at a concentration of 100 µg per milliliter, the vancomycin is present at a concentration of 50 µg per milliliter, and the imipenem is present at a concentration of 96 µg per milliliter.

8. The antibiotic cocktail of claim 5 wherein the antibacterial agents further comprise netilmicin.

9. The antibiotic cocktail of claim 8 wherein the vancomycin is present at a concentration of about 50 µg per milliliter, the imipenem is present at a concentration of about 10–100 µg per milliliter, and the netilmicin is present at a concentration of about 20–50 µg per milliliter.

10. The antibiotic cocktail of claim 9 wherein the amphotericin B is present at a concentration of 1.0 μg per milliliter, the fluconazole is present at a concentration of 100 μg per milliliter, the vancomycin is present at a concentration of 50 μg per milliliter, the imipenem is present at a concentration of 96 μg per milliliter, and the netilmicin is present at a concentration of 50 μg per milliliter.

11. A method of decontaminating a tissue for transplantation comprising:

contacting the tissue with the antibiotic cocktail of any one of claims 1–10 at a temperature and for a period of time effective to substantially inhibit yeast and bacterial growth while substantially maintaining the viability of the tissue.

12. The method of claim 11 wherein the tissue is a heart valve, a vessel, pericardium or musculoskeletal tissue.

13. The method of claim 12 wherein the temperature is 35°–39° C. and the period of time is 24–48 hours.

* * * * *